United States Patent [19]
Hescht et al.

[11] Patent Number: 5,212,437
[45] Date of Patent: May 18, 1993

[54] HIGH SPEED STARTER OPERATIONS MONITOR

[75] Inventors: Donald A. Hescht, Clinton; Walter A. Dupuis, Cleveland Heights; William E. Szabo, North Olmstead; Theodore A. Resnick, Beachwood, all of Ohio

[73] Assignee: Picker International, Inc., Highland Hts., Ohio

[21] Appl. No.: 739,837

[22] Filed: Aug. 2, 1991

[51] Int. Cl.[5] .......................... H01J 35/10; H02P 9/12
[52] U.S. Cl. .................................... 318/798; 388/809; 388/811; 378/131; 318/778
[58] Field of Search ............... 318/811, 809, 806, 805, 318/798, 722, 778; 388/811, 819, 829, 831, 911, 809; 310/74; 322/4, 8

[56] References Cited
U.S. PATENT DOCUMENTS

| | | | |
|---|---|---|---|
| 4,172,991 | 10/1979 | Akamatsu et al. | 318/798 |
| 4,355,276 | 10/1982 | Vittay | 310/74 |
| 4,680,525 | 7/1987 | Kobari et al. | 318/798 |
| 4,703,245 | 10/1987 | Sakamoto et al. | 318/798 |
| 4,829,551 | 5/1989 | Resnick et al. | 378/131 |
| 4,904,919 | 2/1990 | McNaughton | 318/798 |

Primary Examiner—William M. Shoop, Jr.
Assistant Examiner—John W. Cabeca
Attorney, Agent, or Firm—Fay, Sharpe, Beall, Fagan, Minnich & McKee

[57] ABSTRACT

An x-ray tube (10) of a CT scanner has a rotating anode and rotor combination which is propelled by AC currents applied to run and phase windings (42, 46) by a starter (22). A monitor (24) includes Hall effect current detectors (40, 44) which detect the actual current flowing through the run and phase windings. The detected analog current values, voltage values, and the like are multiplexed (132) and digitized in a preselected order by an analog to digital converter (60) and stored in that order in a FIFO memory (62). A microprocessor (64) performs a Fourier transform (94, 96) to convert the digital run and phase signals into frequency spectra. The run and phase frequency spectra are compared (100, 102, 104, 106) with frequency spectra indicative of rotor speed, bearing wear, anode vibration, failure of the anode to rotate, and other conditions, analyzed for symmetry or other characteristics, or the like (FIG. 5) to generate digital run and phase reference signals. An error amplifier (54) controls a pulse width modulator (56) or other power amplifier controls in accordance with a deviation between analog reference signals converted from the digital signals by a reference digital to analog converter (66) and the actually sensed run and phase signals (40, 44) to adjust the starter. A direct coupled driver (122) adjusts DC offsets in the drive currents to maintain balance and drive efficiency.

18 Claims, 4 Drawing Sheets

HIGH SPEED STARTER OPERATIONS MONITOR

BACKGROUND OF THE INVENTION

The present invention relates to the art of rotational speed control. It finds particular application in conjunction with controlling the starting and acceleration of rotating anodes in x-ray tubes and will be described with particular reference thereto. However, it is to be appreciated, that the invention may also find application in other fields.

Conventionally, x-ray tubes have a cathode and an anode. The cathode is typically a filament which is heated with a filament current to a sufficient temperature that a cloud of electrons is boiled off. A high x-ray tube voltage or kV is applied between the cathode and anode to cause a flow of the electrons, a tube current, from the cathode to the anode. The electron flow heats the anode to very high temperatures, near its melting point, such that x-rays are generated. To prevent the anode from becoming thermally damaged in high output tubes, the anode is rotated. Commonly, the anode is a disk which is mounted to an inductive rotor. In very high output x-ray tubes, the anode is often 10 or 15 centimeters in diameter. The rotor, its mounting bearings, the anode, and cathode are all sealed within the x-ray tube envelope. Run and phase windings are mounted outside the x-ray tube envelope adjacent the rotor to provide motive rotational forces thereto. In this manner, a non-synchronous type motor is created, which motor is relatively inefficient due to the spacing limitations between the run and phase windings and the rotor imposed by the x-ray tube envelope.

The large anode and relatively high operational speeds tend to cause bearing degradation. Because the bearings are sealed within the x-ray tube envelope, it is important to preserve the bearings for the life of the tube. Accordingly, the rotating anode is commonly rotated at its operating speed for the generation of x-rays and rotated at a slower speed or stopped when no x-rays are being generated. To meet customer demand and to minimize mechanical resonance, the rotor and anode typically accelerate quickly to the operating speed. Typically, an electrical braking force is applied after the x-ray exposure to return the anode more quickly to its idle speed.

Commonly, high speed x-ray tube anode starters use open loop type controls. That is, AC currents of the appropriate phase and frequency to cause rapid acceleration of the rotor are applied to the run and phase windings. In these open loop systems, the laws of electromagnetism are relied upon to assure that the anode actually accelerates as projected.

Other anode starters use closed loop analog circuitry to compare the actual and anticipated rotational speed of the rotor and anode. The speed of the rotor and anode can be determined directly with a tachometer or derived indirectly from the relative phase, frequency, and magnitude of the currents through the run and phase windings. A rotor that is lagging or leading the rotational speed that the phase and frequency of the applied run and phase currents are designed to provide causes measurable alterations in these currents. These measurable differences or analog error signals can control a modulator which in turn controls the AC current pulses applied to the run and phase currents.

Typical prior art rotor speed control circuits are shown in U.S. Pat. No. 4,829,551 issued May 9, 1989 to Messrs, Resnick, Dupuis, and Szabo and U.S. Pat. application Ser. No. 07/489,465 of Rarick. The present invention contemplates a new and improved digital starter speed monitor and control method and apparatus.

SUMMARY OF THE INVENTION

In accordance with one aspect of the present invention, electrical power applied to the run and phase windings of an x-ray tube is monitored during acceleration of the rotor. An analog to digital converter converts the sampled electrical signals to digital format. The digital signals are operated upon and processed digitally in accordance with a preselected algorithm. Output signals are used to control a power supply for supplying electrical power to the run and phase windings in accordance with the analysis.

In accordance with another aspect of the present invention, a multiplexing means is provided for enabling a plurality of analog electrical signals to be digitized serially by the analog to digital converter.

In accordance with another more limited aspect of the present invention, a FIFO memory or register queues data that is sampled by the analog to digital converter. This allows the microprocessor or other control system to perform other duties while additional run and phase data is being sampled.

In accordance with another aspect of the present invention, the digital data is transformed into the frequency domain, such as with a Fourier-type transform. The harmonic content or fingerprint is analyzed in the frequency domain.

One advantage of the present invention is that it enables more precise control and monitoring of the rotation of the x-ray tube anode. Another advantage of the present invention is that it reduces x-ray tube damage by detecting anode rotation related malfunctions more quickly.

Another advantage of the present invention is that the hardware can be updated with new and improved software as it is developed.

Still further advantages of the present invention will become apparent to those of ordinary skill in the art upon reading and understanding the following detailed description.

BRIEF DESCRIPTION OF THE DRAWINGS

The invention may take part in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
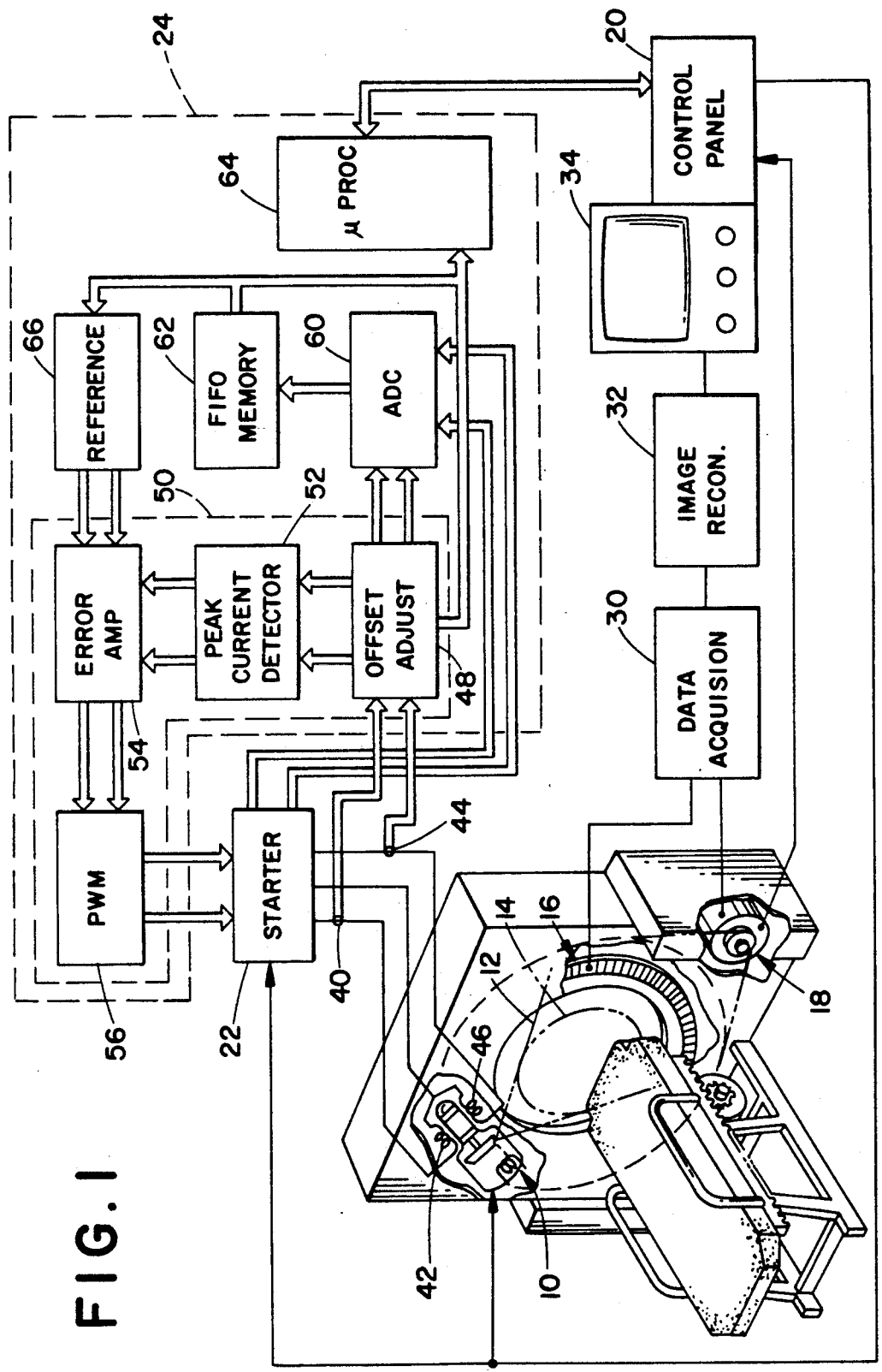
FIG. 1 is a diagrammatic illustration of a CT scanner incorporating an x-ray tube anode speed control monitor in accordance with the present invention.

With reference to FIG. 1, a CT scanner includes a rotating anode x-ray tube 10 which selectively projects a fan-shaped beam 12 of penetrating radiation. The radiation traverses an examination region or image circle 14 and impinges upon an arc of radiation detectors 16. A motor or other means 18 selectively causes relative rotational movement between the radiation beam and a subject in the scan circle. A control panel 20 enables the operator to select various system controls, displays, and events. Among the provided controls on the panel are switches or means for the operator to initiate a CT scan, for selecting x-ray tube operating parameters including tube current and tube voltage, for selecting various display formats, and the like. When a scan is to be initiated, the control panel causes a high speed starter 22 to commence bringing the anode up to the operational rotational speed. Once the anode has been brought to the operating speed, the control panel causes the x-ray tube voltage and filament current to be applied to the x-ray tube for the duration of the selected exposure. After the exposure is completed, the control panel may cause the starter 22 to decelerate the anode. A suitable starter 22 is described in the above-referenced U.S. Pat. application Ser. No. 07/489,465. A starter monitor 24 monitors operation of the starter 22 to determine when the anode has reached its operating speed, if the anode is accelerating normally, whether there are problems, e.g. whether the anode is undergoing excessive vibration or other indications of bearing wear, determines any necessary adjustments for the starter to accelerate the anode more quickly or efficiently, and the like.

Once the anode has reached the selected rotational speed and the x-ray tube voltage and filament current have been applied, the generation of the fan beam 12 commences. Concurrently, the motor 18 causes the x-ray tube, hence the fan beam, to rotate around the subject in the examination circle. The radiation detectors 16 generate output signals indicative of the intensity of radiation received. Of course, the intensity data may be considered as indicative of the absorption or attenuation of radiation along each ray by the subject in the examination region. A data acquisition circuit 30 collects the x-ray intensity data from the detectors. The data acquisition circuit may reorganize the order of the data, e.g. from source fan beam data to detector fan beam data, filter the data with various filters as are conventional in the art, and the like. An image processor 32 performs a filtered back projection or other conventional image reconstruction algorithm to generate an image representation. The image representation may be displayed on a video monitor 34 or other display means, stored on tape or disk, subjected to further processing, or the like.

The starter monitor 24 includes a first current sensor 40 for monitoring current flow through a run coil 42 and a second current sensor 44 for sensing current flow through a phase coil 46. The sensors generate analog run and phase signals indicative of the monitored currents. An offset adjustment 48 calibrates the analog run and phase signals relative to preselected zero or other reference current value.

A current control loop 50 includes a peak current detector 52 which determines the peak amplitude of each cycle of the monitored run and phase currents. An error amplifier 54 determines a difference or error between the actually monitored current peaks and preselected current peaks, e.g. a differential amplifier. A pulse width modulator 56 puts out pulses of selectable width which drive a power amplifier in the starter 22 to produce an output current proportional to the pulse width. The width of the pulses provided by the pulse width modulator is adjusted by the error amplifier 54 such that the error or difference between the desired and monitored currents is adjusted toward zero. More specifically, the error amplifier means includes a pair of error or differential amplifiers, one for the run current and one for the phase current. The error or difference signal for the run current controls a run pulse width modulator and the error or difference in the phase current controls a phase pulse width modulator. The pulse width modulator array 56 controls the run and phase current pulses or oscillations applied by the starter 22.

An analog to digital converter 60 converts the offset adjusted analog run and phase signals from analog to digital format. The analog to digital converter further converts the run and phase currents as generated by the starter 22 from analog to digital. It will be noted that the inductance of the run and phase windings as well as the coupled inductance from the rotor may cause the monitored run and phase signals to differ from the run and phase current which the starter is supplying. For example, the inductive load and the coupling between the inductors will tend to shift the relative phase of the run and phase currents. The analog to digital converter may include an array of converters. However, because the analog to digital conversion time is relatively short compared to the preferred sampling rate, there is preferably a multiplexer which receives the analog signals from the current sensors and the starter and supplies them one by one to a single analog to digital converter.

The digital run values, phase values, and the like are stored in a FIFO memory 62 in the order set by the multiplexer. A microprocessor 64 reads the current values from the FIFO memory 62 and calculates reference run and phase current values, determines if run and phase currents meet selected criteria, and the like. The digital reference run and phase current values are supplied to a reference means 66 which converts the digital reference run and phase current values to analog which the error amplifiers 54 compare with the actually monitored currents from the current peak detector 32. The reference means 66 is continuously updated by the microprocessor. The reference means 66 preferably includes separate run and phase digital to analog converters which each continue to supply an analog value corresponding to the most recently received digital value until next updated. The output analog reference value thus is continuously updated as the microprocessor calculates new reference run and phase current values.

Figures 2, 3:
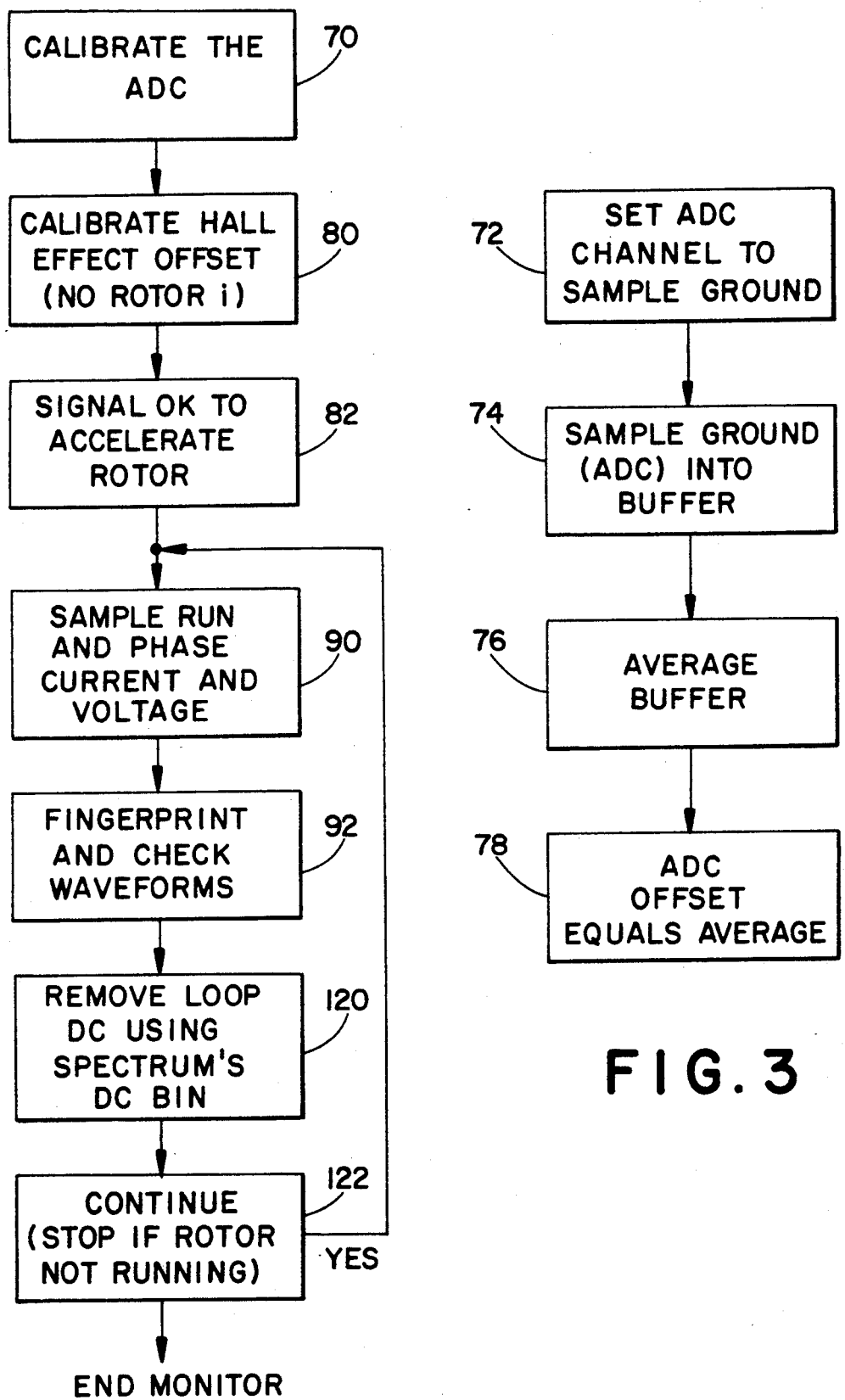
FIG. 2 is a diagrammatic illustration of the analysis of the monitored signals.
FIG. 3 is a more detailed illustration of the calibration step or means of FIG. 2.

With reference to FIG. 2, the microprocessor 64 performs or includes means for performing a step 70 of calibrating the analog to digital converter 60.

With reference to FIG. 3, the analog to digital calibrating step includes a step or means 72 for connecting the analog to digital converter 60 to ground. A step or means 74 samples the grounded or "zero" output a plurality of times and loads the values into a buffer. An averaging means 76 averages the values of the buffer and a step or means 78 sets the analog to digital converter offset value equal to the average.

With reference again to FIG. 2, step or means 80 calibrates the offset adjustment means 48. Generally, the offset adjustment is performed by zeroing the output of Hall effect current sensors 40, 44 while there is no rotor current flowing through the run or phase windings. Calibrating the Hall effect sensors includes removing the heat exchanger current from Hall effect current sensors. The error imbalance is determined, which balance is again a sum between the first and last sample divided by the number of samples. The number of bits of balance error is determined. If the number of bits is greater than zero and less than the maximum range of the system, the offset adjustment means 48 is calibrated, else an error is reported. Once the calibrations have been completed, a step or means 82 signals the starter 22 to commence supplying current to rotate the anode again.

Preferably, the multiplexer and FIFO memories are set up such that the current and voltage of each winding are interlaced or sampled alternately. A run and phase current and voltage sampling means or step 90 samples the digital run and phase current and voltage values from the FIFO memory 62. A step or means 92 fingerprints and checks the current and voltage waveforms. More specifically, with reference to FIG. 4, the fingerprinting and checking step or means includes a step or means 94 for calculating frequency spectra. More specifically, frequency spectra are determined by a step or means 94 for performing a double Fourier transform on the winding current and voltage values. A step or means 96 performs an analogous double Fourier transform on the phase current and voltage values. An unscrambling means or step 98 unscrambles the Fourier transformed pairs into current buffers and voltage buffers. A step or means 100 compares or checks the run winding current spectrum against preselected, acceptable spectra or performs analyses which determine properties of the spectrum and compares the determined properties to like preselected criteria. A run voltage spectrum comparing or checking means or step 102 compares each run voltage spectrum with preselected run voltage spectra or calculates characteristics that are compared to preselected criteria. A phase current spectrum checking means or step 104 compares each phase current spectrum with preselected spectra or Criteria. A phase voltage spectrum checking means 106 compares each phase voltage spectrum with preselected spectra or criteria. The comparing or checking means or steps can also compare the spectra with historical data concerning the spectra of the same winding current or voltage to monitor changes in the spectrum with aging, wear, or other malfunctions. A control signal is supplied to the panel 20 to warn the operator of the malfunction. The comparing steps may compare the whole spectrum, key frequencies or frequency bands, or the like.

Figures 4, 5:
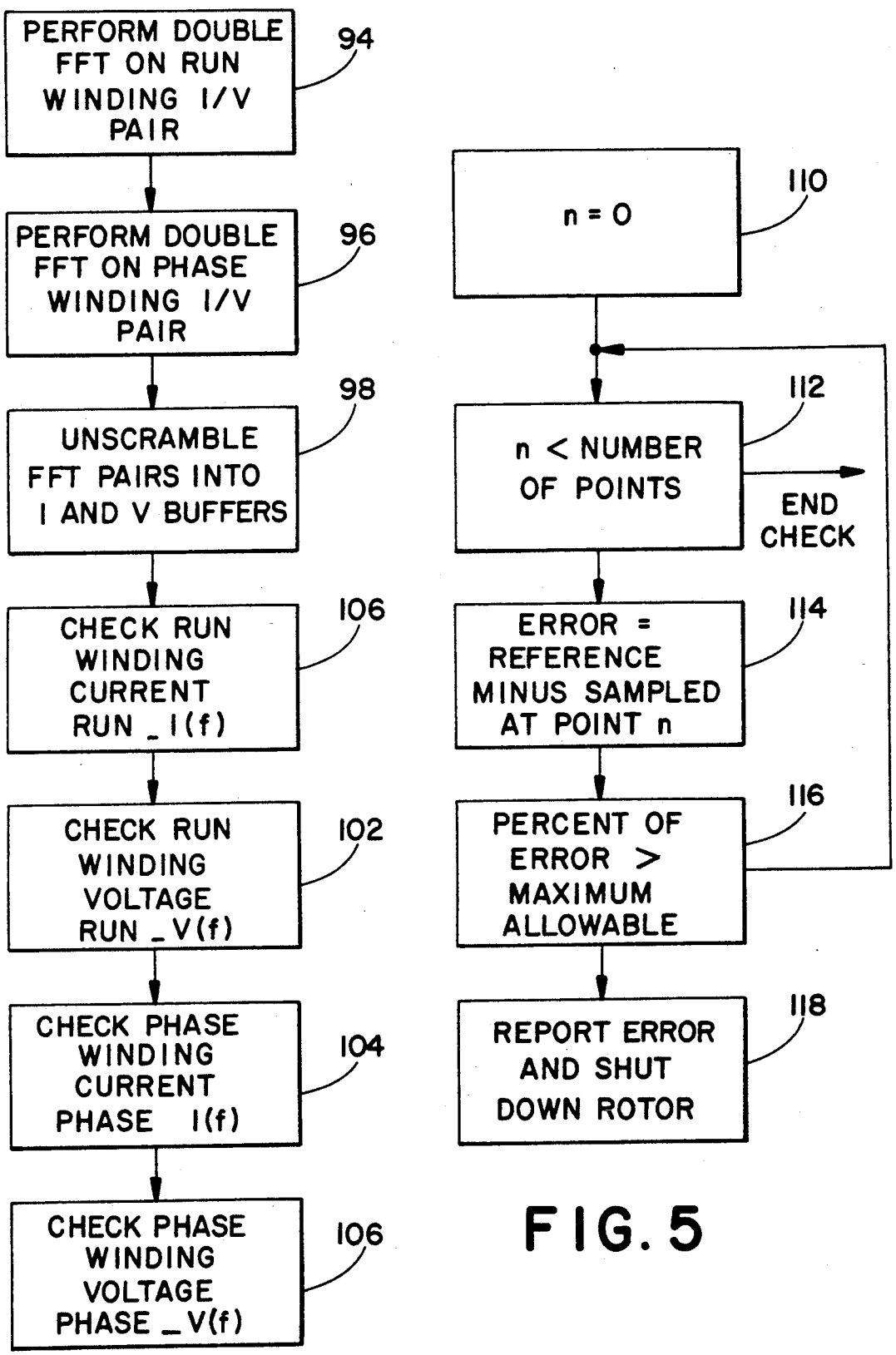
FIG. 4 is a more detailed explanation of the spectrum computation step or means of FIG. 2.
FIG. 5 is a more detailed illustration of the spectrum or fingerprint analyses step or means of FIG. 2.

With reference to FIG. 5, the spectrum comparing or checking steps 100, 102, 104, and 106 each include a step or means 110 which indexes n, where "n" is a number of a point sampled in each spectrum. An end of comparison step or means 112 compares n with the number of the points to be sampled. If n exceeds the number of sampled points, the end of the comparison is signaled and the comparison of the next spectrum started. If the comparison is continuing, a step or means 114 determines the deviation error, i.e. the reference value minus the sampled value at each analyzed point n of the spectrum. The error from each analyzed spectrum component is used to generate a digital deviation or error signal. For example, the n error values for the analyzed spectrum can be used as an n bit address for a look-up table that is preprogrammed to retrieve a corresponding digital deviation signal that increments or decrements the reference signal of the reference means 66. Alternately, the n error values can be analyzed in other ways to generate the deviation signal. For example, the spectrum can be analyzed for a center frequency, a shift in the center or average frequency, the amplitude of defect indicating frequencies, and the like. By way of more specific example, the monitor performs a winding status check function. The monitored winding current and voltage values are loaded into a memory array. A frequency spectrum of each voltage and current value is determined. The frequency equals the inverse of a total time between the first and last zero crossing divided by the total number of cycles. If the frequency is incorrect, then a frequency error is reported. Next, an average current is determined. The average is the sum of the absolute value of each corresponding monitored current value divided by the number of points between the first and last zero crossing. If the average current is off by more than a preselected percentage, then a current error or deviation is reported. A balance error is determined by summing the monitored points between the first and last zero crossing and dividing by the number of samples. If the balance is higher than a preselected maximum, a balance error is reported to the control panel.

A percentage of error determining step or means 116 determines the percentage of error and compares the percentage with a maximum allowable percentage. If the percentage is within tolerances, the microprocessor 64 increments n and returns to step 112 to determine whether or not all of the points of the spectrum have been analyzed. If the percentage of error is greater than the maximum allowable, then a step or means 118 reports the error to the control panel 20 causing the exposure to be terminated and rotation of the rotor to cease.

With reference again to FIG. 2, a step or means 120 increments the reference means 66. More specifically to the preferred embodiment, the reference means 66 is a digital to analog converter and the means 120 adjusts the offset to the digital to analog converter in accordance with the comparison of the sampled and preselected spectrums in order to determine the reference value used by the error amplifier means 54. A step or means 122 determines from the spectrum analysis whether or not the rotor is spinning and corrects DC offsets. If the rotor is being spun, then the step or means 122 causes the microprocessor to continue to step through the sampling and analysis steps described above. The means 122 includes a direct coupled driver that corrects for DC offsets in the drive currents and magnets to maintain balance and drive efficiency. If the rotor is no longer running, then the monitoring process is terminated or ended.

When the command is given on the operator panel 20 to commence exposure, the run and phase loops are calibrated. The power to the starter 22 is turned on. If the starter power and status are incorrect, then an error is noted by the monitor 24 and the procedure is stopped. If the power and status are correct, the current for each winding is selected by the microprocessor 64 and applied by the starter 22 to the windings. The monitor 24 monitors the applied currents. If the monitored currents indicate a malfunction, then the procedure is terminated. If the rotor is not accelerating as fast as it should, the monitor adjusts the reference value, i.e. the target values for the run and phase currents. After the rotor reaches a selected operating speed, the monitor 24 shifts modes from monitoring the rotor acceleration to monitoring whether the rotor is maintaining the selected rotational speed.

In the run or operating state, the monitor 24 periodically cycles through its checking routine. It first checks the status of the run and phase windings. If either is incorrect and indicates a malfunction, then the malfunction is reported to the control panel. Further, the monitor determines whether the filament is on, as well as whether current is being applied to the rotor. If no filament current is being applied, i.e. no x-rays are being generated, then the rotor is turned off. That is, the control panel is caused to terminate the application of electrical power to the run and phase windings.

Figure 6:
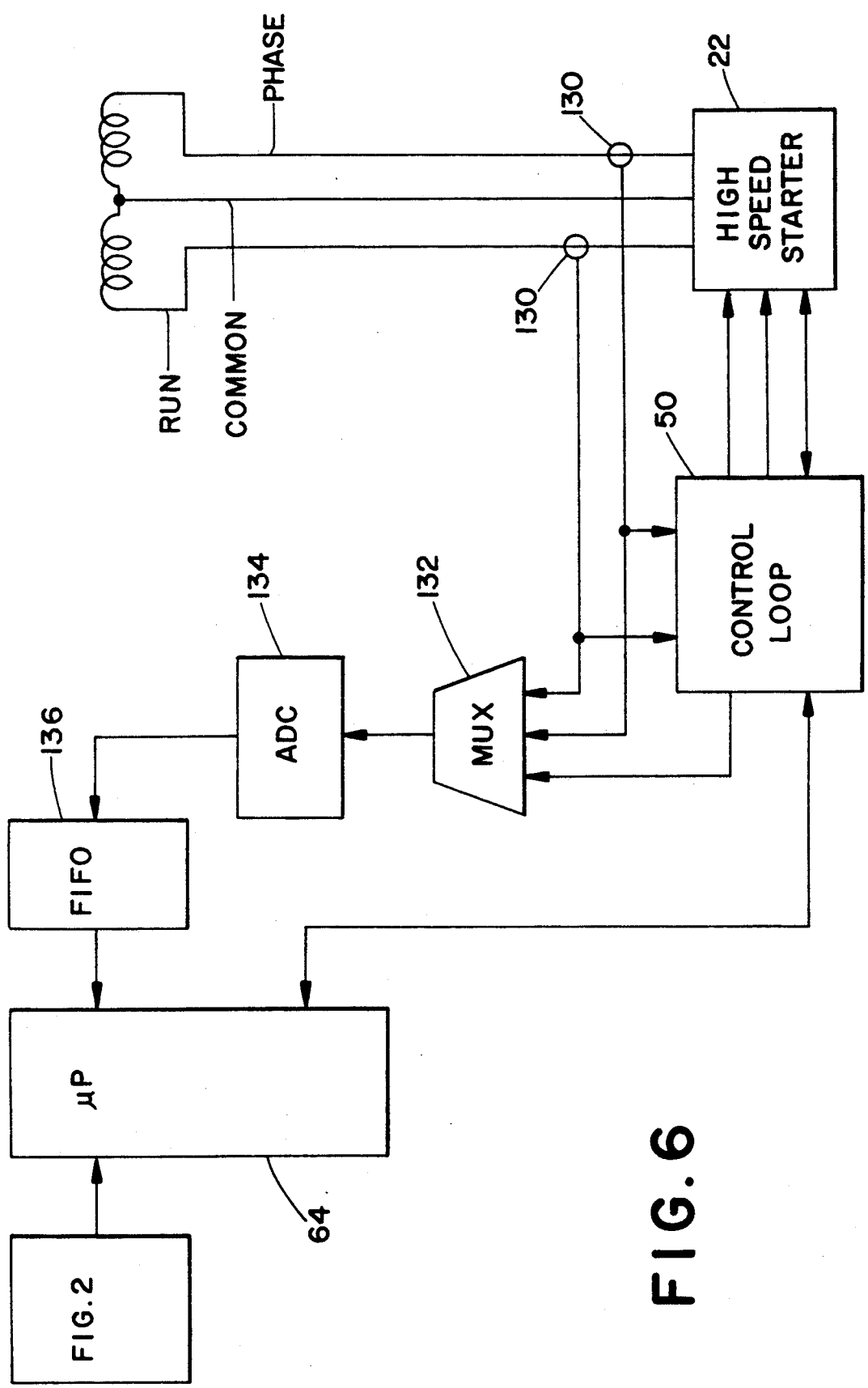
FIG. 6 is a diagrammatic illustration of an alternate embodiment of the system of FIG. 1.

With reference to the alternate embodiment of FIG. 6, a pair of current sensors 130 monitor analog current flow from the starter 22 to the run and phase stator windings. A multiplexer 132 cyclically feeds the analog current signals and analog voltage signals from the sensors and from a control loop 50 to an analog to digital converter 134. The analog to digital converter digitizes each of its received signals and temporarily stores the digital signals in a FIFO memory means 136. A microprocessor 64 withdraws the digital values from the FIFO memory and operates on them with preselected algorithms to derive appropriate control instructions for the control loop 50. For example, the microprocessor may compare the phase of the run and phase currents to be sure that one is leading the other by a preselected angular increment. Preferably as discussed above, the sampled current signals are converted to the frequency domain creating an array of frequency spectrums or fingerprints. The frequency components and their relative amplitude are indicative of many conditions, such as acceleration torque, rotation of the rotor, bearing wear, anode vibration, and the like. The harmonic content of these spectrums varies with the type of x-ray tube, particularly the diameter of the anode, the type of bearings, the relative number of windings in the phase and run windings, and the like. Accordingly, the footprint or frequency component amplitude characteristics indicative of the various characteristics and problems in this embodiment is preferably determined by trial and error. That is, by monitoring the fingerprint of one or more x-ray tubes of the given style and configuration, appropriate fingerprint ranges are determined for each of the characteristics and problems. The microprocessor compares the monitored fingerprint against these premeasured fingerprint characteristics.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An apparatus for monitoring operation of an x-ray tube rotor in which run and phase windings provide motive power to the x-ray tube rotor, the apparatus comprising:

an electric supply means for supplying electrical currents to the run and phase windings;

a sensor means for sensing at least the electrical currents supplied to the run and phase windings and providing analog sensor signals indicative thereof;

an analog to digital converter means for converting the analog sensor signals to digital sensor signals;

a microprocessor means for processing the digital sensor signals and deriving digital reference signals therefrom, the microprocessor means including:
 a means for converting the digital sensor signals into digital frequency spectra,
 a fingerprint means of comparing the digital frequency spectra with a preselected frequency spectra criteria to monitor for wear and malfunctions;

a digital to analog converter means for converting the digital reference signals to analog reference signals, the digital to analog converter means being operatively connected with the processor to receive the digital reference signals therefrom and operatively connected with the electric supply means.

2. An apparatus for monitoring operation of an x-ray tue rotor in which run and phase windings provide motive power of the x-ray tube rotor, the apparatus comprising:

an electric supply means for supplying electrical currents to the run and phase windings;

a sensor means or sensing at least the electrical currents supplied to the run and phase windings and providing analog sensor signals indicative thereof;

an analog to digital conveyor means for converting the analog sensor signals to digital sensor signals;

a microprocessor means for processing the digital sensor signals and deriving digital reference signals therefrom;

a digital to analog converter means for converting the digital reference signals to analog reference signals;

a control loop mans for comparing the analog sensor signals with the analog reference signals, the control loop means being connected with the supply means for controlling supply means in accordance with the comparison of the analog reference and sensor signals, the control loop means being connected with the sensor means and with the digital to analog converter.

3. The apparatus as set forth in claim 2 wherein the control loop means includes:

a peak current detector for detecting peak run and phase currents from the analog sensor signals;

a comparing means or comparing the run and phase peak currents with the analog reference signals from the digital to analog converter and providing run and phase error signals indicative of the deviation therebetween;

a pulse width modulator means controlled by the run and phase error signals for modulating widths of pulses supplied by the supply means to the windings.

4. The apparatus as set forth in claim 3 wherein the digital sensor signals include at least digital run and phase signals and wherein the processor means further includes:

a means for transforming the digital run and phase signals to run and phase frequency spectrums;

a means for comparing the run and phase frequency spectrums with preselected frequency spectrum criteria;

means for generating the digital reference signal in accordance with the frequency spectrum comparisons.

5. The apparatus as set forth in claim 4 wherein the means for transforming the run and frequency signals to spectra includes a Fourier transform mean for performing a Fourier transform on the digital run and phase signals.

6. An apparatus for monitoring cooperation of an x-ray tube rotor in which run and phase windings provide motive power to the x-ray tube rotor, the apparatus comprising:

an electric supply means for supplying electrical power to the run and phase windings;
a run current sensor for sensing the electrical power supplied to the run winding and generating run sensor signals;
a phase sensor for sensing electrical power supplied to the phase winding and generating phase sensor signals;
a multiplexing means for supplying at least the run and phase sensor signals sequentially;
an analog to digital converter means for receiving the run an phase sensor signals sequentially form the multiplexing means and converting the analog sensor signals to digital sensor signals;
a first in, first out memory means for storing the digital signals from the analog to digital converter means, the digital signals being stored sequentially in the same order that the multiplexing means supplies the analog signals to the analog to digital converter means;
a microprocessor means for processing the digital sensor signals from the fist in, first out memory means and deriving digital reference signals therefrom;
a digital to analog converter means for converting the digital reference signals to analog reference signals; and
an analog feed back lop for comparing the run and phase sensor signals with the analog reference signals and controlling the electric supply means in accordance with the comparison.

7. The apparatus as set forth in claim 2 further wherein the sensing means includes a pair of Hall effect current sensors and an offset adjustment means operatively connected with the Hall effect sensor for providing an offset adjustment to the analog sensor signals therefrom and supplying the offset adjusted analog sensor signals to the analog to digital converter.

8. An apparatus for monitoring operation of an x-ray tube rotor in which run and phase windings provide motive power to the x-ray tube rotor, the apparatus comprising:

an electric supply means for supplying electrical currents to the run and phase windings;
a sensor means or sensing at least the electrical currents supplied to the run and phase windings and providing analog sensor signals indicative thereof;
an analog to digital converter means for converting the analog sensor signals to digital sensor signals;
a means for calibrating the analog to digital converter;
a means for calibrating the sensor means when no current is being supplied to the run and phase windings;
a means for enabling the supply means to commence supplying current to the run and phase windings;
a processor means for converting the digital sensor signals into digital reference signals;
a digital to analog converter means for converting the digital reference signals to analog reference signals, the digital to analog converter means being operatively connected with the processor means to receive the digital reference signals therefrom and operatively connected with the electric supply means.

9. An apparatus for monitoring operation of an x-ray tube rotor in which run and phase windings provide motive power to the x-ray tube rotor, the apparatus comprising:

an electric supply means for supplying electrical currents to the run and phase windings;
a sensor means or sensing at least the electrical currents supplied to the run and phase windings and providing analog run and phase signals indicative thereof;
an analog to digital converter means for converting the analog run and phase signals to digital run and phase signals;
a means for converting the digital run and phase signals to run and phase frequency spectra;
a means for comparing the run and phase frequency spectra with preselected frequency spectrum criteria;
a means for generating a digital reference signal in accordance with the frequency spectrum comparisons;
a digital to analog converter means for converting the digital reference signal to ana analog reference signal, the digital to analog converter means being operatively connected with the digital reference signal generating means to receive the digital reference signal therefrom and operatively connected with the electric supply means.

10. The apparatus as set forth in claim 9 wherein the analog to digital converter means converts the run and phase analog signals to the digital run and phase signals in preselected order and further including as FIFO memory means for storing the digital run and phase signals in the preselected order, the FIFO memory means being accessed by the processor means to receive the digital run and phase signals therefrom.

11. A CT scanner comprising:

an x-ray tube for generating a beam of x-rays, the x-ray tube including a rotating anode connected with a rotor, a run winding, and a phase winding;
an array of radiation detectors for detecting radiation from the x-ray tube that has traversed an examination region;
a rotating means for rotating the x-ray tube around the examination region;
an image reconstruction means for reconstructing spherical signals from the radiation detectors into an image representation;
a current supply means for supplying run and phase AC electrical currents to the run and phase windings, respectively;
a sensor means for monitoring the run and phase currents and producing analog run and phase signals;
an analog loop means for comparing the analog run and phase signals with reference signals and controlling the current supply means in accordance therewith;

an analog to digital converter means for generating digital run and phase signals from the monitored run and phase signals;

a means for comparing the digital run and phase signals with preselected characteristics including at least one of symmetry, frequency, and amplitude, and generating run and phase deviation signals in accordance therewith;

a digital to analog converter means for converting the digital run and phase deviation signals to the reference signals, the digital to analog converter means being operatively connected with the analog loop means.

12. A CT scanner comprising:

an x-ray tube for generating a beam of x-rays, the x-ray tube including a rotating anode connected with a rotor, a run winding, and a phase winding;

an array of radiation detectors for detecting radiation from the x-ray tube that has traversed an examination region;

a rotating means for rotating the x-ray tube around the examination region;

an image reconstruction means for reconstructing electrical signals from the radiation detectors into an image representation;

a current supply means for supplying run and phase AC electrical currents to the run and phase windings, respectively;

a sensing means for monitoring the run and phase currents;

an analog to digital converter means for generating digital run and phase signals from the monitored run and phase currents;

a transform means for transforming the digital run and phase signals to frequency spectra;

a means for comparing the digital run and phase frequency spectra with preselected characteristics including at least one of symmetry, frequency, and amplitude, and generating run and phase deviation signals in accordance therewith;

a digital to analog converter means for converting the digital run and phase deviation signals to analog run and phase reference signals, the digital to analog converter means being operatively connected with the current supply means for causing the run and phase currents supplied thereby to be adjusted in accordance with the reference signals.

13. The scanner as set forth in claim 12 further including:

a means for comparing the sensed, analog run and phase currents with the reference signals;

a pulse width modulator controlled by the means for comparing the analog reference signals and the monitored run and phase currents and for modulating widths of pulses supplied to the current supply means.

14. A method of monitoring operation of a rotor of an x-ray tube, the method comprising:

supplying AC electrical power to run and phase windings of the x-ray tube;

sensing at least the electrical power flowing through each of the run and phase windings and providing analog sensor signals indicative thereof;

converting the analog sensor signals to digital sensor signals;

processing the digital sensor signals and deriving digital reference signals therefrom;

converting the digital reference signals to analog reference signals;

controlling the supply of AC electrical power to the run and phase windings in accordance with the reference signals;

transforming the digital sensor signals to frequency spectra; and comparing the frequency spectra with predetermined frequency spectra criteria to determined wear and malfunction information.

15. An method of monitoring operation of a rotor of an x-ray tube, the method comprising:

supplying AC electrical power to run and phase windings of the x-ray tube;

sensing at least the electrical power flowing through each of the run and phase windings and providing analog sensor signals indicative thereof;

comparing the analog sensor signals with an analog reference signal and controlling the supply of AC electrical power to the run and phase windings in accordance with a deviation therebetween;

converting the analog sensor signals to digital sensor signals;

processing the digital sensor signals and deriving digital reference signals therefrom;

converting the digital reference signaled to the analog reference signal.

16. A method of monitoring operation of a rotor of an x-ray tube, the method comprising:

supplying AC electrical power to run and phase windings of the x-ray tube;

sensing at least the electrical power flowing through each of the run and phase windings and providing analog sensor signals indicative thereof;

converting the analog sensor signals to digital sensor signals;

transforming the digital sensor signals to frequency spectra;

comparing the frequency spectra with preselected frequency spectra criteria;

generating a digital reference signal in accordance with the frequency spectra companions;

converting the digital reference signal to analog reference signal;

controlling the supply of AC electrical power to the rim and phase winding in accordance with the reference signal.

17. A method of monitoring operation of a rotor of an x-ray tube, the method comprising:

supplying AC electrical power to windings of the x-ray tube;

sensing at least the electrical power flowing through the windings and providing analog sensor signals indicative thereof;

multiplexing the analog sensor signals;

converting the multiplexed analog sensor signals from analog to digital sequentially;

temporarily storing the digital sensor signals in the same order as they are multiplexed;

processing the stored digital sensor signals on a first in, first out basis to derive digital reference signals therefrom;

converting the digital reference signals to analog reference signals;

controlling the supply of AC electrical power to the run and phase windings in accordance with the analog reference signals.

18. The method as set forth in claim 15 wherein the processing step further includes:

comparing the digital sensor values with preselected sensor values to determine a deviation therebetween; and incrementing the reference signal in accordance with the deviation.

* * * * *